United States Patent
Goldau et al.

[11] Patent Number: 6,126,831
[45] Date of Patent: Oct. 3, 2000

[54] METHOD AND DEVICE FOR DETERMINING HEMODIALYSIS PARAMETERS

[75] Inventors: Rainer Goldau, Werneck; Matthias Krämer, Oberursel, both of Germany

[73] Assignee: Fresenius Medical Care Deutschland GmbH, Bad Homburg, Germany

[21] Appl. No.: 09/133,252

[22] Filed: Aug. 13, 1998

[30] Foreign Application Priority Data

Aug. 13, 1997 [DE] Germany .............................. 197 34 992
Feb. 19, 1998 [DE] Germany .............................. 198 06 900

[51] Int. Cl.[7] ................................................. B01D 61/34
[52] U.S. Cl. ................... 210/646; 210/96.2; 210/321.65; 210/739; 210/929; 604/4.01
[58] Field of Search ................... 210/85, 87, 94, 210/96.2, 138, 321.65, 321.69, 321.71, 416.1, 646, 647, 739, 746, 929, 637, 745; 604/4–6, 4.01, 5.01, 6.01, 6.09, 6.15

[56] References Cited

U.S. PATENT DOCUMENTS

| | | | |
|---|---|---|---|
| 4,923,613 | 5/1990 | Chevallet | 210/647 |
| 5,110,477 | 5/1992 | Howard et al. | 210/647 |
| 5,744,031 | 4/1998 | Bene | 210/646 |
| 5,849,179 | 12/1998 | Emerson et al. | 210/646 |
| 5,938,938 | 8/1999 | Bosetto et al. | 210/646 |

FOREIGN PATENT DOCUMENTS

| | | |
|---|---|---|
| 0 291 421 B1 | 11/1988 | European Pat. Off. . |
| 0 330 892 A2 | 9/1989 | European Pat. Off. . |
| 0 547 025 B1 | 6/1993 | European Pat. Off. . |
| 0 578 585 B1 | 1/1994 | European Pat. Off. . |
| 428 927 A1 | 5/1991 | Germany . |
| WO 94/08641 | 4/1994 | WIPO . |
| WO 94/09351 | 4/1994 | WIPO . |

OTHER PUBLICATIONS

Sargent JA, Gothch FA: Principles and Biophysics of Dialysis, in: W. Drukker et al., eds *Replacement of Renal Function by Dialysis*, Nijhoff, The Hague 1983. pp 53–96.

Nguyen Khoa Man et al., "Clinical Validation of a Predictive Modeling Equation for Sodium" Artificial Organs 9(2): (1985) Raven Press, New York. pp 150–154.

*Primary Examiner*—Joseph W. Drodge
*Attorney, Agent, or Firm*—Kenyon & Kenyon

[57] ABSTRACT

A device and method are described to determine the concentration of a substance in blood flowing through a blood chamber of a dialyzer during extra corporeal blood treatment. The flow rate of dialysate flowing through the dialysate chamber of the dialyzer is reduced to a value at which the concentration of the substance at the outlet of the dialysate chamber is essentially the same as the concentration of that same substance in the blood at the inlet of the blood chamber. The concentration measurement can be carried out without interrupting the flow of dialysate.

28 Claims, 4 Drawing Sheets

METHOD AND DEVICE FOR DETERMINING HEMODIALYSIS PARAMETERS

FIELD OF THE INVENTION

The present invention relates to a method and device for determining hemodialysis parameters during extracorporeal blood treatment.

RELATED TECHNOLOGY

An important function of human kidneys is the excretion, from the blood, of metabolic products eliminated in the urine and adjustment of water and electrolyte elimination. Hemodialysis is a method of treatment designed to compensate for renal dysfunction in elimination of metabolic products eliminated in the urine and adjustment of the electrolyte concentration in the blood. Water elimination is controlled during the procedure by an ultrafiltration device.

During hemodialysis, blood is directed to an extracorporeal circulation path through the blood chamber of a dialyzer; the blood chamber is separated from a dialysate chamber by a semipermeable membrane. The dialysate chamber is fed with dialysate containing blood electrolytes in a specified concentration. The concentration in the dialysate ($c_d$) corresponds to the concentration in the blood of a healthy person. During treatment, the patient's blood and the dialysate are passed by both sides of the membrane, usually in countercurrent, at a predetermined flow rate ($Q_b$ or $Q_d$, respectively). The metabolic products eliminated in the urine diffuse through the membrane from the blood chamber to the dialysate chamber, while at the same time the electrolytes present in the blood and in the dialysate diffuse from the chamber of higher concentration to the chamber of lower concentration. The metabolism can also be influenced by applying transmembrane pressure.

To optimize the blood treatment method, hemodialysis parameters must be determined during the extracorporeal procedure (in vivo). Of particular interest is the value for the concentration of a substance in the blood at the dialyzer inlet, or the exchange efficiency of the dialyzer for a specified substance, represented by "clearance" or "dialysance D."

Clearance for a specified substance K denotes the virtual (calculated) blood volume from which a specified substance is removed completely in the dialyzer per minute under defined conditions. Dialysance is another term for determining the efficiency of a dialyzer, which takes into account the concentration of the eliminated substance in the dialysate. In addition to these dialyzer performance parameters, other parameters are also important, such as the values of the aqueous portion of the blood, the blood volume and the concentration in the blood at the inlet, etc.

It is a relatively complex matter to quantify blood purification methods mathematically on the basis of measurement technology and to determine the above-mentioned dialysis parameters. A basic measurement reference work in this regard is Sargent JA, Gotch FA: Principles and Biophysics of Dialysis, in: W. Drukker, F. M. Parsons, J. F. Maher eds. *Replacement of Renal Function by Dialysis*, Nijhoff, The Hague 1983.

Dialysance or clearance for a given electrolyte, e.g., sodium, at the zero ultrafiltration rate is determined as follows: The dialysance D is equal to the ratio between the mass transport for this electrolyte on the blood side ($Q_b \times (c_{bi} - c_{bo})$) and the difference in concentration of this electrolyte between the blood and the dialysate at the inlet of the dialyzer ($c_{bi} - c_{di}$):

$$D = Q_b \cdot \frac{c_{bi} - c_{bo}}{c_{bi} - c_{di}} \quad (1)$$

On the basis of mass balance:

$$Q_b \cdot (c_{bi} - c_{bo}) = -Q_d \cdot (c_{di} - c_{do}) \quad (2)$$

It follows from equations (1) and (2) above that:

$$D = Q_d \cdot \frac{c_{do} - c_{di}}{c_{bi} - c_{di}} \quad (3)$$

where in equations (1) through (3):
D=dialysance
$Q_b$=effective blood flow
$Q_d$=dialysate flow
$c_{do}$=the concentration of the substance in the dialysate flowing out of the dialysate chamber
$c_{di}$=the concentration of the substance in the dialysate flowing into the dialysate chamber
$c_{bo}$=concentration of the substance in the blood flowing out of the dialysate chamber
$c_{bi}$=the concentration of the substance in the blood flowing into the blood chamber The effective blood flow is the flow of the blood portion in which the substances to be removed are dissolved, i.e., it is based on the (aqueous) solution volume for this substance. Depending on the substance, this may be the plasma water flow or the blood water flow, i.e., the total amount of water in whole blood. The concentration cb refers to the relevant blood portion.

In the case of a specific metabolic waste product (e.g., urea), $c_{di}=0$ since this substance for purposes of determination is not present in the fresh dialysate. Then dialysance is no longer spoken of, but instead of the clearance K for this product of metabolism:

$$K = Q_b \frac{(c_{bi} - c_{bo})}{c_{bi}} = Q_d \frac{c_{do}}{c_{bi}} \quad (4)$$

Previous methods of in vivo determination of hemodialysis parameters are based on the above considerations. It is desirable to avoid direct measurement of the blood side because such measurement could represent a source of considerable risk. Therefore, the values that are to be determined must be derived solely from measurements on the dialysate side European Patent No. 0 291 421 B1 discloses a method of determining the concentration in the blood at the inlet $c_{bi}$, by which the inlet dialysate concentration is varied ramp-wise to determine the point at which there is no further transfer of electrolyte across the membrane. Therefore, the method works according to the principle of varying the inlet conductivity of the dialysate to the extent that it no longer differs from the outlet conductivity. It must then be equal to the inlet conductivity of the blood ($c_{bi}=c_{di}$). Other hemodialysis parameters can then be derived on the basis of equations (1) through (3), such as the value of D or $Q_b$. A disadvantage of this method is the relatively long measurement time, due to the time interval required to reach a stable steady state during adjustment of the dialysate to the new input concentration value, which is not immediately effective at each point in the dialyzer. The system requires a certain amount of time before an increase in conductivity at the dialysate inlet leads to stable conditions at the dialysate outlet. The time interval required to reach a stable steady state is basically determined by the size of the variation in conductivity per unit of time. Within this long time interval, however, the dialysis parameters can change and thus falsify the value to be determined.

It should be noted in particular that the method described above (like other methods) can directly change the concentration in the blood at the inlet $c_{bi}$ through induced electrolyte transfer. In the method described above, this systematic error is especially serious due to the type of change in concentration on the dialysate side. The method thus does not lead to accurate measured values for the hemodialysis parameters to be determined in vivo. In addition, relatively complex additional equipment is required to vary the dialysate concentration at the inlet.

German Patent No. 39 38 662 C2 (related to European Patent Application No. 0 428 927 A1) describes a method of in vivo determination of hemodialysis parameters by which the dialysate electrolyte transfer is measured at two different dialysate concentrations at the inlet. On the assumption that the concentration in the blood at the inlet is constant, dialysance can be determined according to the method by determining the value of the differences in dialysate ion concentration at the inlet and outlet sides of the dialyzer at the time points of the first and second measurements, then by dividing this value by the difference in dialysate ion concentration at the inlet side at the times of the first measurement and the second measurement and then multiplying the resulting quotient by the dialysate flow. This method proves to be disadvantageous to the extent that relatively complex equipment is required for varying the concentration in the blood at the inlet.

European Patent Application Nos. 0 330 892 A1 and 0 547 025 describe another method that has as its object the determination of the concentration in the blood at the inlet. The difference in the dialysate ion concentration at the inlet and outlet sides of the dialyzer, i.e., the electrolyte transfer rate, is determined. The known method also works with different concentration settings along the dialysate path, which means that relatively complex equipment is likewise required for varying the dialysate concentration at the inlet.

U.S. Pat. No. 5,110,477 discloses a method of determining the clearance of a dialyzer by which calibration solutions are passed through the dialyzer on both the dialysate side and the blood side. This method also requires relatively complex equipment and in addition cannot be performed in vivo but only in vitro, i.e., outside the ongoing dialysis treatment.

International Patent Application No. WO 94/09351 describes a urea sensor for a hemodialysis device that removes the dialysate to be used for analysis from the dialysate path. The sampling of dialysate assumes a set flow rate in the dialysate.

A method for determining the sodium concentration in the blood circulation of an artificial kidney is described in an article by Nguyen Khoa Man et al., "Clinical Validation of a Predictive Modeling Equation for Sodium," published in Artificial Organs 9(2):150–154 (1985), Raven Press, New York. Measurement occurs in the dialysate circuit. According to the method, the dialysate circuit conduction leading to and from the dialyzer is short-circuited sufficiently to permit only a small amount of dialysate to be pumped through the dialyzer by the dialysate pump. This results in the establishment of a steady state and the concentration values in the blood circulation correspond to those in the dialysate circuit.

European Patent No. 0 578 585 B1 also discloses a method by which measurement on the dialysate side occurs after establishment of a steady state. In this method also only a small amount of dialysate recirculates through the dialyzer until a steady state has been established.

Methods which allow only a small amount of dialysate to be passed through the dialyzer during measurement are disadvantageous to the extent that they require rerouting of the dialysate in the dialysate path. This involves investment in additional equipment.

In addition, previous hemodialysis devices are provided upstream and downstream from the dialyzer dialysate chamber with stopcocks and a bypass line that bridges the path through the dialyzer dialysate chamber for the purpose of performing leak tests on the dialyzer.

International Patent Application No. WO 94/08641 describes a monitoring system for a hemodialysis device with a urea sensor that is arranged in the dialysate path. The documentation proposes short-circuiting the inlet and outlet of the dialyzer dialysate chamber by means of a bypass for a predetermined time interval of approximately 5 minutes so that circulation of dialysate through the dialysate chamber will be interrupted. Although the dialysate flow is interrupted, ultrafiltration must still be maintained. When the predetermined time interval has elapsed, a sample is taken at the outlet of the dialysate chamber that can be used for determination of the dialyzer clearance.

SUMMARY OF THE INVENTION

An object of the present invention is to provide a method of determining hemodialysis parameters during extracorporeal blood treatment that permits a simple measurement on the dialysate side of the concentration of a substance in the blood, the substance being part of the materials exchanged in the dialyzer. The substance concentration measured may be a parameter to be determined itself, or an intermediate value for a parameter to be determined during.

The present invention therefore provides a method for determining hemodialysis parameters during an extracorporeal blood treatment in which the blood to be treated in an extracorporeal blood circulation flows at a preset blood flow rate through the blood chamber of a dialyzer. The dialyzer is divided by a semipermeable membrane into a blood chamber and a dialysate chamber, and the dialysate in a dialysate path flows through the dialysate chamber of the dialyzer at a preset dialysate flow rate. The method comprises the following series of steps: setting the dialysate flow rate $Q_d$ to a value at which the concentration $c_{do}$ of a substance in the dialysate flowing from the dialysate chamber substantially adopts the concentration $c_{bi}$ of the substance of interest in the blood flowing into the blood chamber; and measuring the concentration of the substance in the dialysate flowing from the dialysate chamber, the substance being the parameter to be determined or an intermediate value for a parameter to be determined.

Another object of the present invention is to create a blood treatment device with a mechanism for determination of hemodialysis parameters during extracorporeal blood treatment that permits a very simple measurement on the dialysate side of the concentration of a substance in the blood, which is part of the exchange of materials in the dialyzer. The substance concentration measured may be a parameter to be determined itself, or an intermediate value for a parameter to be determined.

The present invention therefore provides a blood treatment device with a dialyzer (7) provided with a blood chamber (4) connected to an extracorporeal blood circulation (2), which is separated by a semipermeable membrane (5) from a dialysate chamber (6) connected to a dialysate path (1). A blood pump (9) is connected to the extracorporeal blood circulation and a dialysate pump (13) is connected to the dialysate path. A mechanism is provided for determining hemodialysis parameters during extracorporeal blood treatment, the mechanism comprising a measuring device (16) arranged in the dialysate path (1) downstream from the dialysate chamber (6) for measuring the concentration $c_{do}$ of the substance in the dialysate flowing from the dialysate chamber. A control unit (21) is provided, the control unit being designed in such a way that the capacity of the dialysate pump (13) during the dialysis treatment can be reduced from a preset value for a preset time interval to a value at which the concentration $c_{do}$ of the substance in the dialysate flowing from the dialysate chamber as measured with the measuring device (16) substantially adopts the concentration $c_{bi}$ of the substance of interest in the blood flowing into the blood chamber (4). An analyzer unit (19) is provided, the analyzer receiving the output signal of the measuring device (16) that is controlled by the control unit (21) in such a way that the analyzer unit records the concentration $c_{do}$ of the substance of interest as the parameter to be determined or as an intermediate value for a parameter to be determined before the control unit raises the capacity to its original value.

Surprisingly, it was determined that if the flow rate of the dialysate flowing through the dialysate chamber is reduced to a specific value starting from a given value for the blood treatment, the concentration of a substance in the dialysate flowing from the dialysate chamber of the dialyzer substantially adopts the concentration of the substance of interest in the blood flowing into the blood chamber for the most part independently of the blood treatment conditions. Accordingly, it is not necessary to interrupt the dialysate flow through the dialysate chamber in order to establish a steady state. Even under variable treatment conditions, the concentration of a substance at the dialyzer blood chamber inlet can be determined with adequate precision by measuring the concentration of the substance at the outlet of the dialysate chamber whenever the dialysate flow rate is reduced during extracorporeal treatment. When the concentration in the blood at the inlet, i.e., the concentration of a substance in the blood flowing into the dialyzer blood chamber, has been determined, by measurement of the concentration of the dialysate at the outlet, i.e., the concentration of a substance in the dialysate flowing from the dialysate chamber, as a parameter to be determined or as an intermediate value for a parameter to be determined, then the dialysate flow rate can be preset at a predetermined value for the blood treatment. This offers the advantage that not only is a limited sample volume made available, but also the fluid leaving the dialysate chamber can be maintained at the concentration level to be measured for precisely the time interval needed for the measurement. Ongoing ultrafiltration is not required to obtain the sample volume since the measurement can only occur if equilibrium is established by diffusion. Thereby, the method according to the present invention can also be used in situations where continuation of ultrafiltration would lead to a critical condition for the patient. Apart from this, ultrafiltration may be continued at any time as a support for the measurement procedure.

Another advantage offered is that treatment can be continued during the measurement procedure, although less efficiently. A further advantage is that the dialyzer or the membrane can be flushed out or rinsed off, thereby preventing residue from appearing in the dialyzer during the measurement procedure.

Setting the dialysate flow rate to a value at which the concentration of the substance in the dialysate chamber essentially adopts the concentration of the same substance in the blood can be done at the beginning or end of the treatment or while it is still in progress. The reduced dialysate rate can be set at the same time as the initial measurement so that it may be raised later to the treatment value. During blood treatment the dialysate flow rate is reduced, starting from a predetermined value for the treatment, and is restored to its original value once the measurement procedure is complete.

It has been shown that at a blood rate greater than 300 mL/min the dialysate rate needs to be set only to a value less than 100 mL/min in order to establish a steady state that enables measurement at a sufficiently accurate level.

As the blood flow decreases, the dialysate rate should be set to a lower value. At a blood flow rate greater than 150 mL/min adequate equilibrium is established when the dialysate rate is set at less than 75 mL/min.

In actual practice, it was found that an adequate steady state was, surprisingly, always possible independently of treatment conditions, e.g., blood flow level or dialyzer membrane size, whenever the dialysate rate was set at 40–60 ml,/min, preferably 50 ml,/min. Only in exceptional cases is it necessary to set a dialysate flow rate of 10–30 mL/min, preferably 20 mL/min.

The preset time interval for establishing a steady state can lie in the range of 1–5 minutes. This setting interval, however, can also be reduced by other measures, such as pressure pulses on the dialysate path and/or parallel ultrafiltration. In addition, extrapolation of the end value on the basis of measurements is possible within a shorter time interval. Such methods are applied, for example, in electronic fever thermometers.

Another object of the present invention is to provide a method of in vivo determination of hemodialysis parameters that permits quick and easy measurement on the dialysate side of the blood concentration of a substance, which is part of the materials exchanged in the dialyzer, to represent directly a parameter to be determined or an intermediate value for a parameter to be determined, without the patient being subjected to possible stress during the measurement due to fluid deprivation.

In the method of the present invention, the dialysate flow is interrupted through the second dialyzer chamber. To this end, it is not necessary that the dialyzer be completely separated from the dialysate circuit. For example, it is also possible to interrupt only the inflow into the dialyzer.

Surprisingly, it was determined that a steady state can be relatively quickly established by reason of diffusion effects alone at least for part of the volume in the dialysate chamber whenever the second chamber of the dialyzer constitutes a fully closed volume during the measurement, i.e., no ultrafiltrate is removed from the dialysate chamber. Since no fluid is removed from the patient during measurement, the method according to the invention creates no stress for a patient on whom ultrafiltration should not be performed.

Results are adequate when a steady state has been established in part of the volume of the dialysate chamber, e.g., near the dialyzer outlet, where a steady state is first established.

Another benefit afforded by the method according to the present invention is that the stopcocks required for interrupting the inflow and outflow of the dialysate and for the bypass line required for bridging the path through the dialysate chamber are already available in known dialyzers, so that no extensive equipment alterations are required in these units. Thus, it is not necessary, for example, to make provision in the dialysate circuit for valve configurations which permit recirculation of the dialysate through the dialyzer. This results in a simple design.

In the method according to the present invention the blood concentration of a substance that is part of the exchange materials in the dialyzer is quickly and easily determined by a short interruption of the dialysis since the dialysate remaining in the dialyzer is permitted to come into equilibrium by diffusion with the blood. After the steady state establishment period has elapsed, the device is again switched over to normal operation and the concentration of the substance in the portion of dialysate still remaining in the dialyzer after disconnection is determined after a set time delay at the site of the concentration measurement sensor that is in any case available and arranged downstream on the dialysate side.

Testing has shown that establishment of a steady state occurs very quickly—in the course of a few minutes. Interruption of dialysis for this extremely brief time, therefore, does not disturb the dialysis treatment and permits a very quick and easy measurement on the dialysate side of the blood concentration of the substance of interest.

Flushing out the residue of the dialysate from the second chamber is performed by reopening the flow path through the second chamber of the dialyzer and expelling the residue with the dialysate flowing into the second chamber. In this way a very easy measurement procedure is achieved. But it is also possible to suction out the dialysate residue from the second chamber with the use of the dialysate pump before restoring the dialysate path.

The measured inlet concentration in the blood of the substance of interest can directly represent a hemodialysis parameter to be determined. It can also serve as an intermediate value for other hemodialysis parameters to be determined. Therefore, it is also possible, for example, according to another embodiment of the present invention, to determine the dialysance D as a parameter whenever the dialysate flow ($Q_d$) and the concentrations of the dialysate at the inlet and outlet of the dialyzer ($c_{di}$ and $c_{do}$, respectively) are measured after removal of the residue from the dialysate circuit and after determining the concentration in the blood at the inlet ($c_{bi}$) as an intermediate value and after dialysis has been switched on again, using the equation:

$$D = Q_d \cdot \frac{(c_{do} - c_{di})}{c_{bi} - c_{di}}$$

The preset interval for establishing the steady state is preferably in the range of 1–3 minutes. To increase the accuracy at intervals of 1–2 minutes, it is expedient also to calculate an expression for the expected end value using the measurement curve gradient so that it becomes possible to work with a shorter interval.

Concentration measurement is preferably performed, as is customary, by conductivity measurement.

Using the device according to the present invention the dialysance of the dialyzer may be obtained in vivo in a very quick and simple manner by, in addition, according to a further embodiment of the invention: a signal in the control/analyzer unit circuit for the value of the concentration of the dialysate upstream and downstream from the dialyzer and a signal for the dialysate flow are switched on; the timing control in the control/analyzer unit circuit is set in such a way that, after measurement of the concentration in the blood at the inlet ($c_{bi}$) and restoration of the dialysate circuit, the signals for the flow ($Q_d$) and for the inlet and outlet concentrations ($c_{di}$ and $c_{do}$, respectively) of the dialysate are analyzed as measurement signals; and the dialysance D is determined from the equation $$D = Q_d \cdot \frac{(c_{do} - c_{di})}{c_{bi} - c_{di}}$$

BRIEF DESCRIPTION OF THE DRAWINGS

Embodiments of the present Invention are described in greater detail below with reference to the drawings, in which.

DETAILED DESCRIPTION

Figure 1:
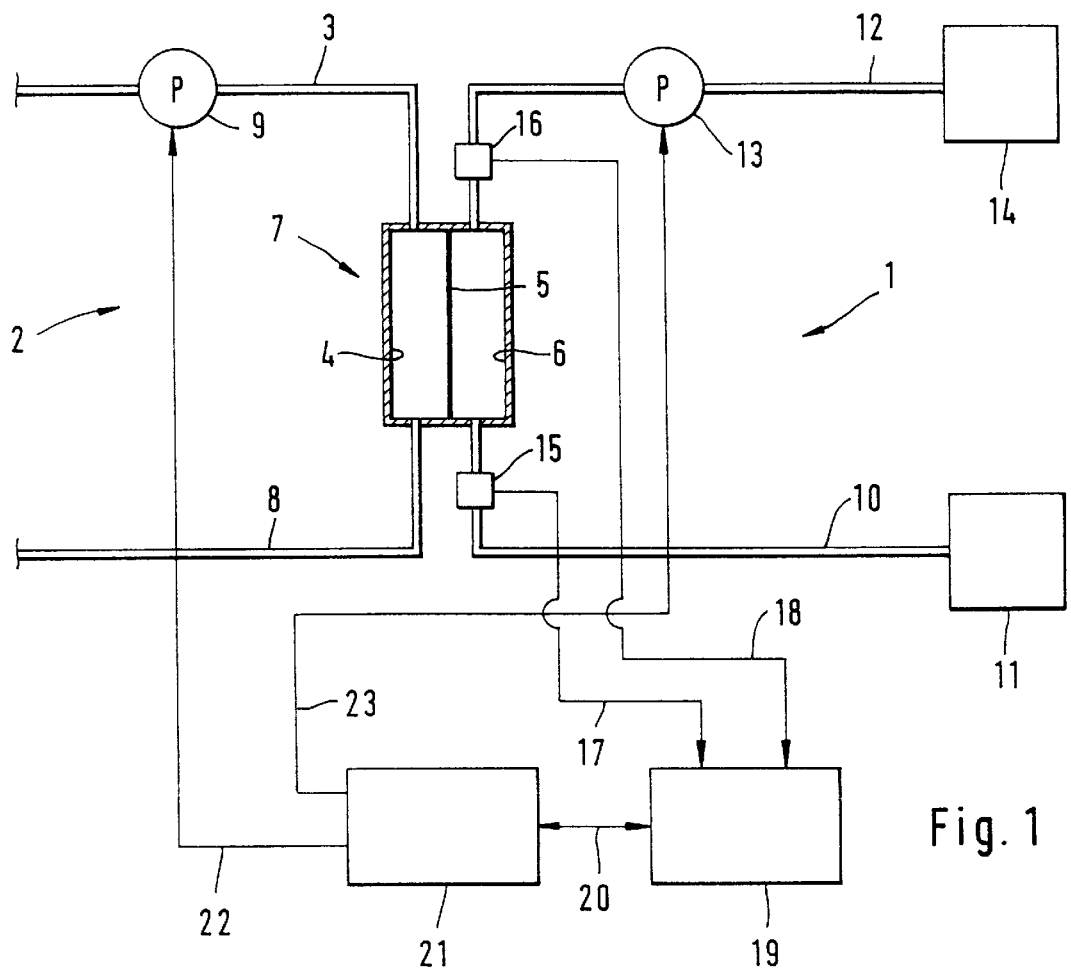
FIG. 1 shows a schematic diagram of a blood treatment device with a mechanism for hemodialysis parameter determination.

In FIG. 1 the key components of a dialysis device are shown. The dialysis device is composed essentially of a dialysate part 1 and an extracorporeal circulation part 2. The extracorporeal blood circulation part, or path, 2 includes an arterial branch 3, a blood chamber 4 of a dialyzer 7 divided by a semipermeable membrane 5 into a blood chamber 4 and a dialysate chamber 6, and a venous branch 8. On the arterial branch 3 a blood pump 9 is arranged through which a set blood flow rate $Q_b$ can be preset in the extracorporeal circulation.

The dialysate chamber 6 of the dialyzer 7 is connected to a dialysate source 11 through a feed line 10. A drain line 12 to which a preset dialysate pump 13 is connected that sets the flow rate $Q_b$ in the dialysate leads to a drain 14.

Measuring devices 15 and 16 of the dialyzer 7 are arranged in both the feed 10 and drain 12 lines for determination of the concentration of the dialysate at the inlet of the dialyzer 7 and the concentration of the dialysate at the outlet of the dialyzer, respectively. The measuring device 15 is not required for executing the method according to the invention. The presence of such a measuring device is advantageous, however, for determining other parameters. The measuring devices 15 and 16 for determining the inlet and outlet concentrations of the dialysate, $c_{di}$ and $c_{do}$ respectively, are provided with conductivity sensors arranged upstream and downstream from the dialyzer 7. The conductivity sensors preferably measure the temperature-corrected conductivity of the dialysate which is primarily required on account of the sodium concentration. Measurement of the dialysate concentration in the dialysate flow path 1 can also be performed by optical and enzymatic sensors, etc., instead of conductivity sensors. Instead of a conductivity sensor, the measuring device 16 may also be provided downstream from the dialyzer 7 with a urea sensor, with omission of a urea sensor upstream from the dialyzer whenever the clearance must be determined. The measuring devices 15 and 16 are connected via data leads 17 and 18, respectively, to an analyzer unit 19 in which the output signals from the measuring devices are processed. The analyzer unit communicates via a data lead 20 with a control unit 21. The control unit 21 is connected to the blood pump 9 and the dialysate pump 13 via control leads 22 and 23 so that the blood flow rate $Q_b$ and dialysate flow rate $Q_d$, respectively, can be set and changed.

During dialysis treatment the dialysate prepared in the dialysate source 11 flows through the dialysate chamber 6 of the dialyzer 7 at a flow rate $Q_d$ preset by the capacity of the dialysate pump 13, while the patient's blood to be treated flows through the blood chamber 4 of the dialyzer 7 at a flow rate $Q_b$ preset by the pump 9.

Execution of the program preset by the control unit 21 for determination of the concentration in the blood at the inlet $c_{bi}$ may be explained as follows:

During hemodialysis treatment the dialysate flow rate is reduced to 40–60 ml,/min, preferably 50 mL/min. Reduction of the flow rate is the result of the control unit 21 appropriately controlling the dialysate pump 13. After elapse of an interval of 2–3 minutes, which is preset by a timing element provided in the control unit, the control unit directs the analyzer unit 19 in such a way that the analyzer unit detects the concentration of the dialysate at the outlet $c_{do}$ which has been measured with the measuring device 16. The measured concentration of the dialysate at the outlet $c_{do}$ corresponds essentially to the concentration in the blood at the inlet $c_{bi}$, the parameter to be determined. In addition, the control unit 21 restores the dialysate flow rate to its original value by means of the dialysate pump 13.

The concentration in the blood at the inlet $c_{bi}$ obtained as described above can serve as an intermediate value in obtaining other parameters. Thus, the dialysance of the dialyzer 7 can be obtained by two further measurements. In this case, the control unit 21 directs the analyzer unit 19 to obtain the inlet dialysate concentration $c_{di}$ that had been measured by the measuring device 15 at a preset dialysate flow rate $Q_d$ and the now-available concentration of the dialysate at the outlet $c_{do}$ which had been measured by the measuring device 16. The analyzer unit determines the dialysance D from the previously determined concentration in the blood at the inlet $c_{bi}$ and the concentrations of the dialysate at the inlet and outlet, $c_{di}$ and $c_{do}$, respectively, as well as from the preset dialysate flow rate $Q_d$, using the equation $$D = Q_d \cdot \frac{c_{do} - c_{di}}{c_{bi} - c_{di}}$$

The parameters to be determined may be displayed on a monitor and/or employed for further process control.

The method according to the present invention is based on the possibility, even under variable treatment conditions, of determining the concentration in the blood at the inlet during reduction of the dialysate flow rate, provided that the concentration of the dialysate at the outlet is measured. This offers the advantage of eliminating the need for intervention in the extracorporeal blood circulation.

The accuracy of the measurement procedure has been verified by the following experiments:

The coupled dialysate and blood circulation were simulated using two peristaltic hose pumps. Since the diffusion action and dialyzer clearances for electrolyte and urea are almost identical, sodium chloride was used instead of urea as a test substance. Thereby, using conductivity measurement, a simple but highly accurate method for concentration measurement is available. On the blood side, 15 mmol NaCl was used. This concentration lies within the range of typical urea concentration. On the dialysate side, pure water was used. The conductivity measurement sensors were placed upstream and downstream of the dialysate chamber of the dialyzer.

The measurements were performed with different types of dialyzer that differ from one another in their membrane surface areas. Measurement curves for several blood flows were obtained for each dialyzer. A minimum blood flow of 200 mL/min was set, which is commonly used under clinical conditions. For a set blood flow rate $Q_b$, the dialysate flow rate $Q_d$ was ramped down from 500 mL/min to 0 mL/min, during which procedure the establishment of a steady state was awaited after each change of dialysate flow $Q_d$. The ratio of dialysate-side conductivity to blood-side conductivity was then determined.

Figure 2C:
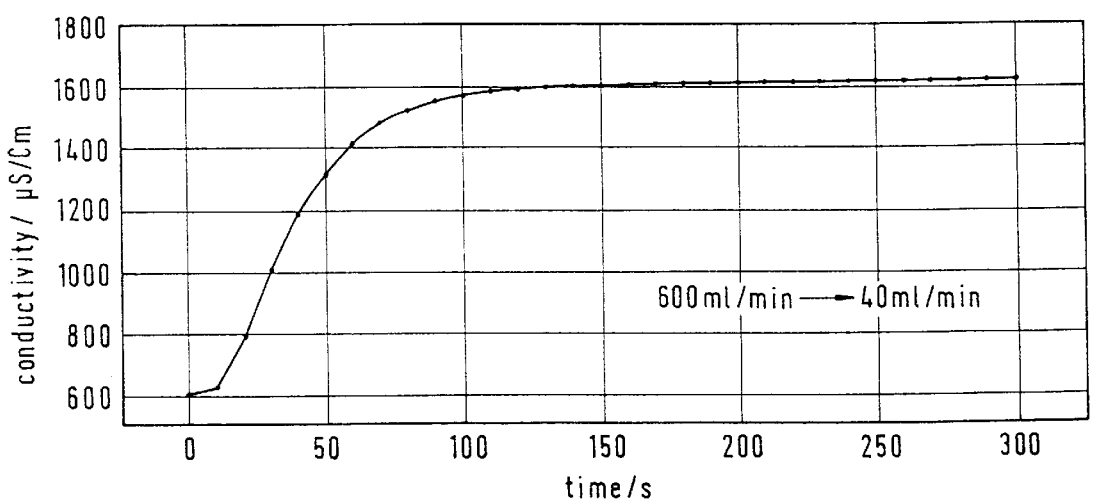
FIG. 2c shows a graph in which the change over time of the dialysate-side conductivity is presented as a result of a change in the dialysate flow rate.
Figure 2A:
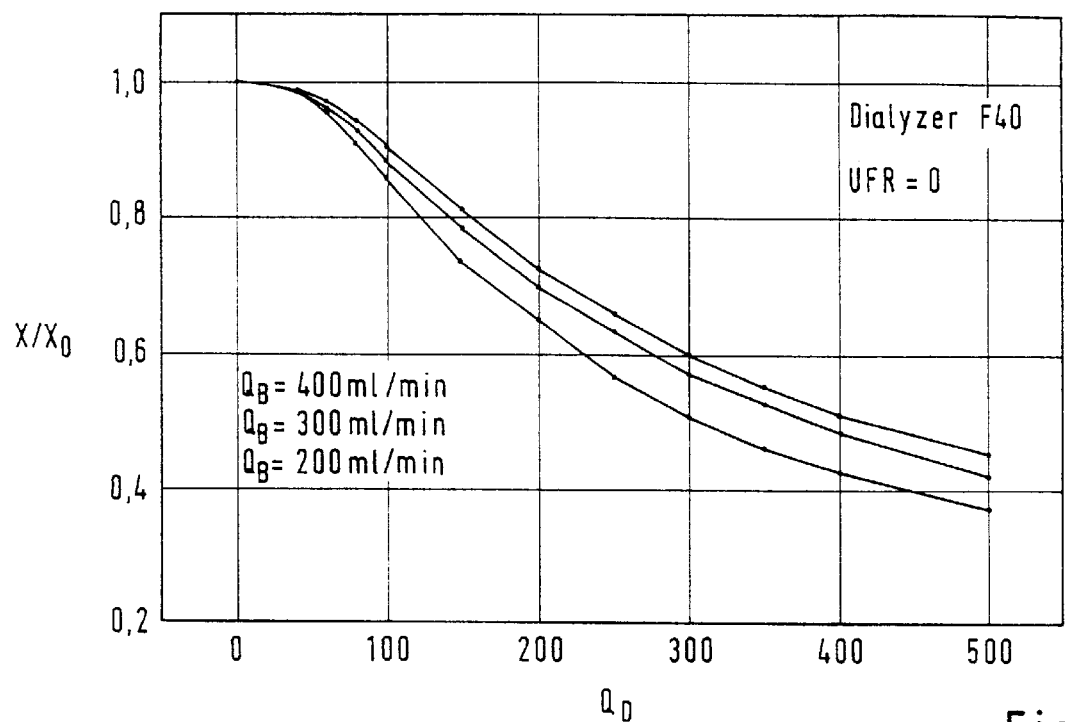
FIG. 2a shows a graph in which the measured ratio between the dialysate-side conductivity and blood-side conductivity in a dialyzer with a 0.7 m² membrane surface area is presented as a function of the dialysate flow rate.
Figure 2B:
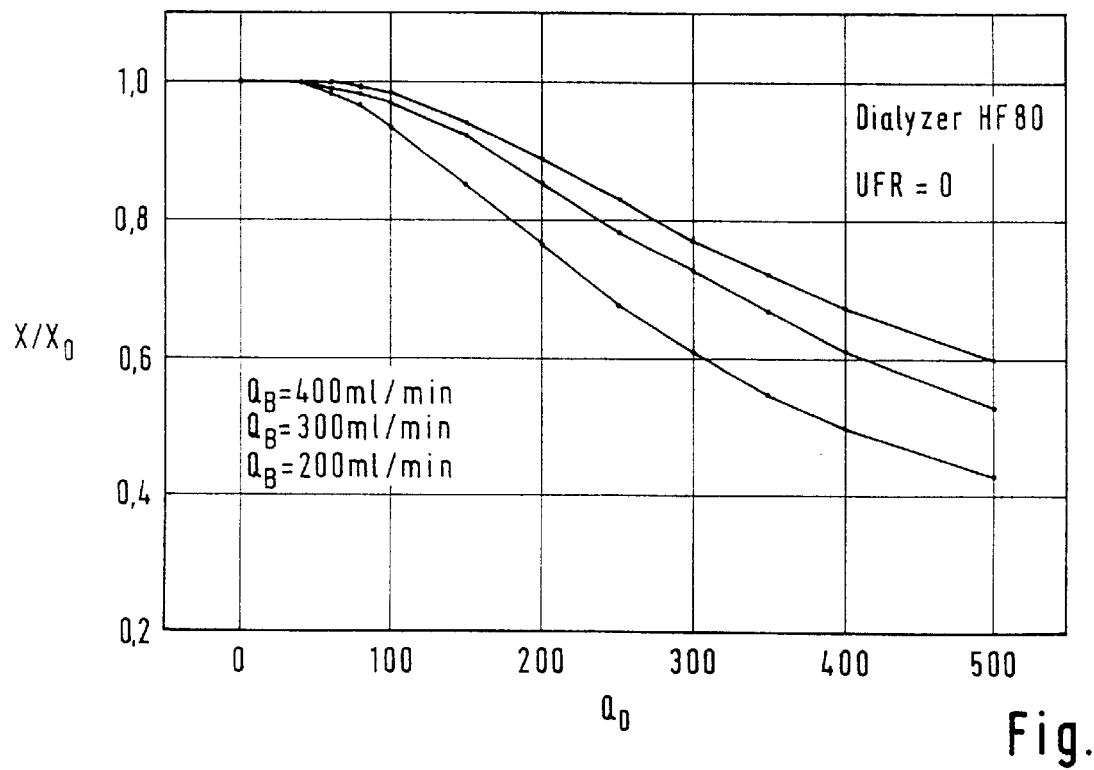
FIG. 2b shows a graph in which the measured ratio between the dialysate-side conductivity and blood-side conductivity in a dialyzer with a 1.8 m² membrane surface area is presented as a function of the dialysate flow rate.

FIG. 2a shows the $X/X_0$ ratio between the dialysate-side and blood-side conductivity as a function of the dialysate flow rate $Q_d$ in a dialyzer with a membrane surface area of 0.7 $m^2$, while FIG. 2b shows the $X/X_0$ ratio between the dialysate-side to blood-side conductivity as a function of the dialysate flow rate $Q_d$ in a dialyzer with a membrane surface area of 1.8 $m^2$. The dialysate-side and blood-side conductivity correspond to the concentration of the dialysate at the outlet and the blood concentration at the inlet, respectively. FIG. 2c shows change over time of the dialysate-side conductivity, and indicates when steady state is reached. As the measurements show, a steady state is almost perfectly achieved with a dialysate flow rate $Q_d$ of 50 mL/min. In a dialyzer with a membrane surface of 0.7 $m^2$ the $X/X_0$ ratio is greater than 0.97 at $Q_b$ greater than or equal to 200 mL/min. In a dialyzer with a membrane surface of 1.8 $m^2$ the $X/X_0$ ratio is greater than 0.99 at $Q_b$ greater than or equal to 200 mL/min. At higher blood flow rates an even better concentration balance is obtained.

Figure 3:
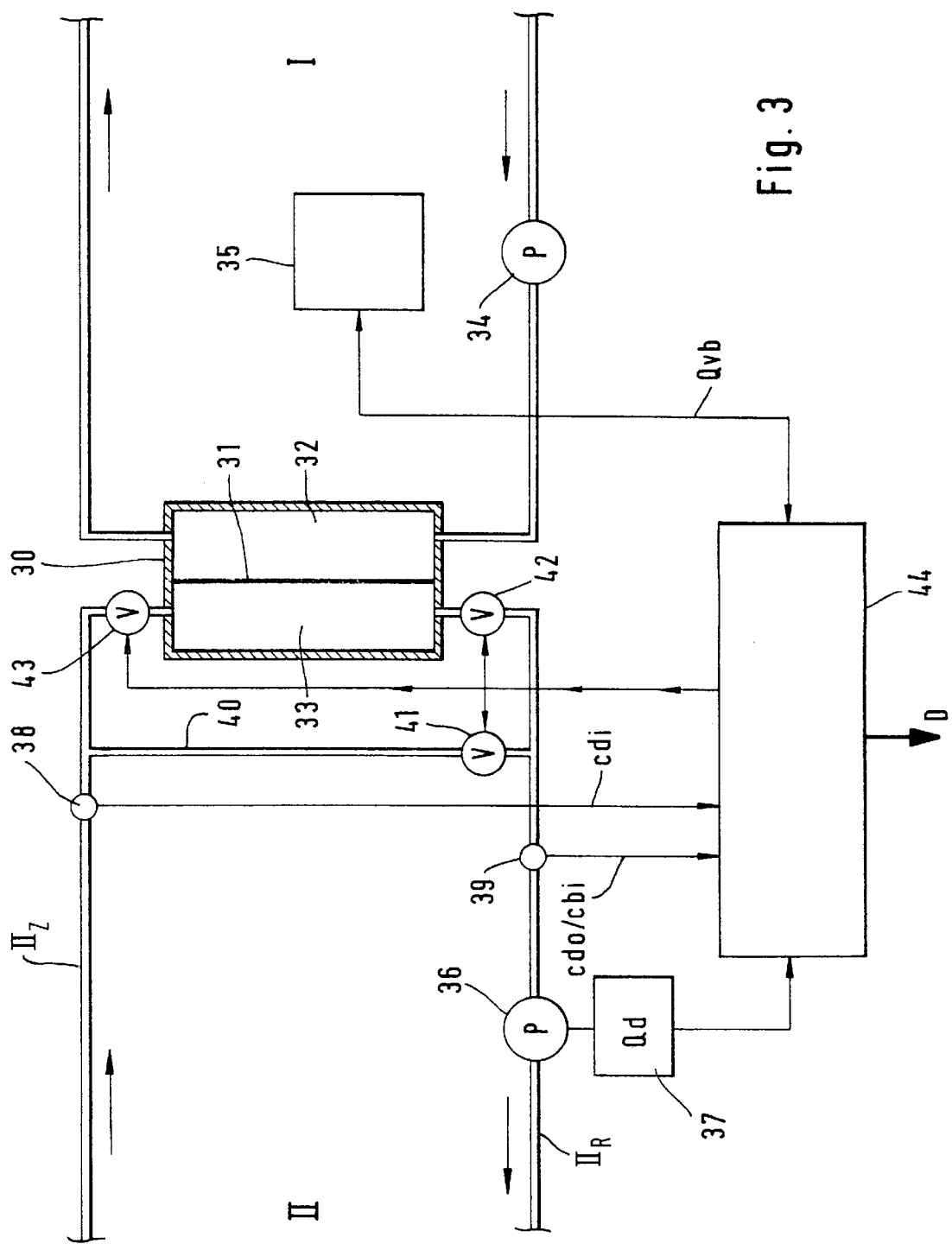
FIG. 3 shows a schematic diagram of a further embodiment of a device for in vivo determination of hemodialysis parameters without the patient being subjected to possible stress during the measurement due to fluid deprivation.

FIG. 3 shows a schematic diagram of a device according to the present invention, with which the method according to the present invention for in vivo determination of hemodialysis parameters is performed without the patient being subjected to possible stress due to fluid deprivation during the measurement.

The device includes a dialyzer 30 with a semipermeable membrane 31 that separates a blood chamber 32 from a dialysate chamber 33. The blood chamber 32 is connected to an extracorporeal circulation path I in which the dialysis patient's blood to be cleaned flows at a flow rate preset by a blood pump 34. A device 35 is provided, through which the rotational speed of the blood pump 34, and thereby the whole blood flow rate $Q_{vb}$, can be changed. These devices are state of the art, as indeed the further design of the extracorporeal circulation I is state of the art, and therefore are not illustrated in the basic schematic diagram according to FIG. 3.

Dialysate chamber 33 is connected to a dialysate circuit II of conventional design. The illustration, for the sake of clarity, contains only one dialysate pump 36, connected to return flow conduit $II_R$, along with its associated mechanism 37 for changing the rotational speed of this pump. Also illustrated are the conductivity sensors 38 and 39 connected, respectively, in input line $II_z$ and the return line of the dialysate circuit II. The conductivity sensors preferably measure the temperature-corrected conductivity of the dialysate on the basis of the sodium concentration. Instead of determining the conductivity, the concentration measurement can also be performed by measuring appropriate optical properties.

The device also includes bypass line 40, bypass valve 41 and two dialyzer cut-off valves 42 and 43.

The remaining design of the device may be as described, for example, in European Patent No. 0 97 366 cited above. The dialysate flows during dialysis operation through the dialysate chamber 33 at a flow rate $Q_d$ preset by the rotational speed of the pump 36, and at an inlet concentration $c_{di}$ set by the concentrate mixture, the inlet concentration being detected by the conductivity sensor 38 arranged upstream. The outlet concentration $c_{do}$ occurring during the dialysis is detected by the downstream conductivity sensor 39. The electrolyte transfer can then be calculated from the $c_{di}$-$c_{do}$ difference. In principle, the conductivity sensor 38 can be omitted and the measured value replaced by a preset value, i.e., a predetermined value, of $c_{di}$. By closing valves 42 and 43 the dialyzer 1 can be disconnected from the dialysate circuit II, with the result that the dialysate flows through the bypass line 40, bypassing the dialyzer when the valve 41 is opened.

All signals for the flow rates $Q_b$ and $Q_d$ and for the concentrations $c_{di}$ and $c_{do}$ on the dialysate side are sent to control/analyzer unit stage 44. Control/analyzer unit Stage 44 is preferably provided with a microprocessor which is usually already present in a dialysis machine. In control/analyzer unit stage 44, the signals are linked together to determine the desired hemodialysis parameters. Thus, for example, the electrolyte transfer rate $Q_d$ X ($c_{di}$-$c_{do}$) is calculated in control/analyzer unit stage 44, and the relationship to other variables is established on the basis of the mass balance in the dialyzer. Control/analyzer unit stage 44 is additionally linked via control leads to the valves 41, 42 and 43.

The basis for in vivo determination of hemodialysis parameters according to the present invention is the determination of the concentration of a substance in the blood of the dialysis patient, the substance being part of the exchange of materials in the dialyzer 30, the so-called concentration in the blood at the inlet $c_{bi}$. This concentration in the blood at the inlet can itself be a parameter to be determined or it can also serve as an intermediate value for a parameter to be determined.

Figure 4:
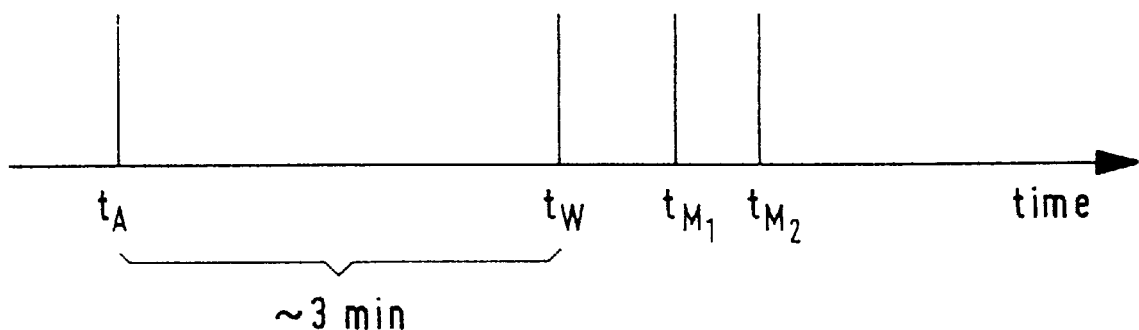
FIG. 4 shows a timing diagram for controlling the measurement function during the dialysis operation of the device shown in FIG. 3.

To determine the $c_{bi}$ value, a control component in the control/analyzer unit stage, activated manually by a staff assistant or is software-driven at time point $t_A$ (FIG. 4), sends a switching signal to the valve arrangement 41, 42, and 43 so that the dialyzer 1 is disconnected from the dialysis circuit II by closure of valves 42 and 43, and bypass line 40 is activated by opening of valve 41. The blood flow in the extracorporeal circulation path I is in this way not interrupted. The residual amount of dialysate in the dialysate chamber 33, an amount greater than 100 mL in conventional dialyzers, is then subjected for a set time to the exchange of materials with the blood flowing in the blood chamber until a steady state has been achieved between the fluid concentrations in both chambers, i.e., the remaining dialysate in the dialysate chamber has adopted the concentration in the blood at the inlet $c_{bi}$ or the inlet conductivity of the blood.

Since the dialysate chamber of the dialyzer constitutes a fully closed volume, no ultrafiltration takes place during measurement. As experiments have shown, this steady state is achieved after only about 3 minutes. When this interval has elapsed, the above-mentioned control component in control/analyzer unit stage 44 sends another signal at time point $t_w$, shown in FIG. 4, by means of a timing switch, which closes the bypass valve 41 and thereby shuts off the bypass line 40 while it also opens valves 42 and 43 and thereby reconnects the dialyzer to the dialysate circuit. The fresh dialysate flowing in then expels the residue in dialysate chamber 33 with its adopted $c_{bi}$ value from this chamber and drives it past conductivity sensor 39. At the correct time point $t_{M1}$, when this residue flows past the conductivity sensor 39 located downstream, the conductivity, and thereby the concentration, is measured and the $c_{bi}$ value determined. The correct time point $t_{M1}$ is determined by determining the dialysate flow interval from the dialyzer 30 to the site of the conductivity sensor 39 with the dialysate circuit in its open state without bypass via the correlation function (determined by removal of the conductivity sensor from the dialyzer and by the dialysate flow-through).

After the bypass 40 is opened and the preset residue from the dialysate circuit II is removed at time point $t_{M2}$, concentrations $c_{di}$ and $c_{do}$ in the dialysate upstream and downstream as well as dialysate flow rate $Q_d$, may be measured, then all measurement values are available to enable determination of dialysance D at control/analyzer unit stage 44 from equation (3) above.

Other parameters of the hemodialysis may be at least estimated by inclusion of a signal relating to whole blood flow $Q_{vb}$.

What is claimed is:

1. A method for determining at least one hemodialysis parameter during an extracorporeal blood treatment using a dialyzer divided by a semipermeable membrane into a blood chamber and a dialysate chamber; the method comprising:

passing blood to be treated in an extracorporeal blood circulation path through the blood chamber at a preset blood flow rate;

passing dialysate in a dialysate path from a dialysate source through the dialysate chamber to a drain at a dialysate flow rate;

setting the dialysate flow rate in the dialysate path to a set dialysate flow rate where a concentration of a substance in dialysate flowing out of the dialysate chamber substantially adopts a concentration of the substance in the blood flowing into the blood chamber; and measuring the concentration of the substance in the dialysate flowing out of the dialysate chamber, the at least one hemodialysis parameter being a function of the concentration of the substance in the dialysate flowing out of the dialysate chamber.

2. The method as recited in claim 1 wherein the concentration of the substance in the dialysate flowing out of the dialysate chamber is the at least one hemodialysis parameter.

3. The method as recited in claim 1 further comprising the step of substantially completing the extracorporeal blood treatment before the step of reducing the dialysate flow rate from a first preset value to the set dialysate flow rate.

4. The method as recited in claim 1 wherein the set dialysate flow rate is set at the beginning of a blood treatment and further comprising, after measuring the concentration of the substance in the dialysate flowing out of the dialysate chamber, raising the dialysate flow rate to a first preset flow rate.

5. The method as recited in claim 1 further comprising the steps of starting from a predetermined dialysate flow rate, reducing the dialysate flow rate to the set dialysate flow rate, and restoring the dialysate flow rate to the predetermined dialysate flow rate after measuring the concentration of the substance flowing out of the dialysate chamber.

6. The method as recited in claim 5 further comprising the steps of, after restoring the dialysate flow rate to the predetermined dialysate flow rate, measuring a concentration of the substance flowing into the dialysate chamber, and determining a dialysance D using the equation:

$$D = Q_d \cdot \frac{c_{do} - c_{di}}{c_{bi} - c_{di}}$$

where:
D=dialysance
$Q_d$=the dialysate flow rate
$c_{do}$=the concentration of the substance in the dialysate flowing out of the dialysate chamber
$c_{di}$=the concentration of the substance in the dialysate flowing into the dialysate chamber
$c_{bi}$=the concentration of the substance in the blood flowing into the blood chamber determined in the measuring step.
dialysance D being one of the at least one hemodialysis parameter.

7. The method as recited in claim 1 wherein the concentration of the substance in the dialysate flowing out of the dialysate chamber is measured after establishment of a steady state.

8. The method as recited in claim 7 wherein the steady state is established in a preset time interval in the range of 1 to 5 minutes.

9. The method as recited in claim 1 wherein the set dialysate flow rate is less than 100 mL/min at a blood flow rate greater than 300 mL/min.

10. The method as recited in claim 1 wherein the set dialysate flow rate is less than 75 mL/min at a blood flow rate greater than 150 mL/min.

11. The method as recited in claim 1 wherein the set dialysate flow rate is between 40 and 60 mL/min.

12. The method as recited in claim 11 wherein set dialysate flow rate is 50 mL/min.

13. The method as recited in claim 1 wherein the set dialysate flow rate is between 10 and 30 mL/min.

14. The method as recited in claim 13 wherein the set dialysate flow rate is 20 mL/min.

15. The method as recited in claim 1 wherein the measuring step is performed by measuring a conductivity of the dialysate.

16. A blood treatment device comprising:
a dialyzer including a blood chamber and a dialysate chamber separated by a semipermeable membrane, the blood chamber being connected to an extracorporeal blood circulation path, the dialysate chamber being connected to a dialysate path;
a blood pump connected to the extracorporeal blood circulation path;
a dialysate pump connected to the dialysate path; and
an apparatus for determining at least one hemodialysis parameter during an extracorporeal blood treatment, the apparatus including:
a measuring device disposed in the dialysate path downstream from the dialysate chamber for measuring a concentration of a substance in dialysate flowing out of the dialysate chamber;
a control unit for determining a concentration of the substance in blood flowing into the blood chamber by reducing a pumping rate in the dialysate path of the dialysate pump during the dialysis treatment, for a preset time interval, from a preset value to a reduced pumping rate in the dialysate path at which the concentration of the substance in the dialysate flowing out of the dialysate chamber as measured with the measuring device substantially adopts the concentration of the substance in blood flowing into the blood chamber, and for, after the preset time interval, raising the pumping rate of the dialysate pump to the preset value; and
an analyzer unit for receiving an output signal of the measuring device, the analyzer unit being controlled by the control unit so that the analyzer unit records the concentration of the substance in the dialysate flowing out of the dialysate chamber before the control unit sets the pumping rate of the dialysate pump to the preset value, the at least one hemodialysis parameter being a function of the concentration of the substance in the dialysate flowing out of the dialysate chamber.

17. The device as recited in claim 16 wherein the concentration of the substance in the dialysate flowing out of the dialysate chamber is the at least one hemodialysis parameter.

18. The device as recited in claim 16 wherein the apparatus further includes a second measuring device disposed in the dialysate path upstream of the dialysate chamber for measuring the concentration of the substance in dialysate flowing into the dialysate chamber, the output signal of the second measuring device being received by the analyzer unit for enabling the analyzer unit to be controlled by the control unit so that the analyzer unit records the concentration of the substance in the dialysate flowing into the dialysate chamber and records the concentration of the substance in the dialysate flowing out of the dialysate chamber when the control unit has set the pump pumping rate to the preset value after the preset time interval, and wherein the analyzer unit is capable of determining a dialysance at a preset blood flow rate, using the equation $$D = Q_d \cdot \frac{c_{do} - c_{di}}{c_{bi} - c_{di}}$$

where:
D=dialysance
$Q_d$=the preset value
$c_{do}$=the concentration of the substance in the dialysate flowing out of the dialysate chamber
$c_{di}$=the concentration of the substance in the dialysate flowing into the dialysate chamber
$c_{bi}$=the concentration of the substance in the blood flowing into the blood chamber.

19. A method for determining at least one hemodialysis parameter in vivo based on a concentration of a substance in an extracorporeal blood circulation path connected to a first chamber of a dialyzer, the first chamber being divided by a semipermeable membrane from a second chamber of the dialyzer, a dialysate circuit being connected to the second chamber, the method comprising:
interrupting dialysate flow through the second chamber for a preset time interval to establish a steady state so that dialysate in the second chamber substantially adopts, at least in a partial volume of the second chamber, a concentration of a substance in blood flowing through the extracorporeal blood circulation path into the first chamber, the interrupting of the dialysate flow occurring without an interruption of a blood flow;

flushing out of the second chamber a residual amount of the dialysate in the second chamber of the dialyzer after establishment of the steady state; and measuring the concentration of the substance in the dialysate in the second chamber after the establishing of the steady state by measuring downstream from the dialyzer the concentration of the substance in the residual amount of the dialysate flowing out of the second chamber, the at least one hemodialysis parameter being a function of the concentration of the substance in the second chamber after the establishing of the steady state.

20. The method as recited in claim 19 wherein the concentration of the substance in the second chamber after the establishing of the steady state is the at least one hemodialysis parameter.

21. The method as recited in claim 19 further comprising bridging flow path through the second chamber using a bypass line connected to the dialysate circuit so that no flow passes through the second chamber and dialysate thereafter remaining in the second chamber is maintained in the second chamber.

22. The method as recited in claim 19 wherein the flushing step is carried out by reestablishing flow through the second chamber, and further comprising determining the concentration of the substance in blood flowing into the first chamber using the measured concentration of the substance in the dialysate in the second chamber measured after the establishing of the steady state, the concentration of the substance in blood flowing into the first chamber being one of the at least one hemodialysis parameter; after the flushing step, measuring a dialysate flow rate and a concentration of the substance in the dialysate flowing into and a concentration of the dialysate flowing out of the dialyzer; and, after the flushing step, determining a dialysance using the equation $$D = Q_d \cdot \frac{c_{do} - c_{di}}{c_{bi} - c_{di}}$$

where:

D=the dialysance $Q_d$=the dialysate flow rate $c_{do}$=the concentration of the substance in the dialysate flowing out of the dialysate chamber $c_{di}$=the concentration of the substance in the dialysate flowing into the dialysate chamber $c_{bi}$=the concentration of the substance in the blood flowing into the blood chamber.

23. The method as recited in claim 19 wherein the preset time interval is in the range of 1 to 3 minutes.

24. The method as recited in claim 19 wherein the concentration measuring step is performed by measuring conductivity. concentration of the substance in blood flowing into the blood chamber, of sending a signal to the interrupting device for reconnecting the dialyzer to the dialysate circuit to flush out the residual dialysate, and then, after a time interval determined by a flow rate of the dialysate and a distance of an outlet of the dialyzer from the sensor, of analyzing the output measurement signal of the sensor to determine the concentration of the substance in the residual dialysate.

25. A blood treatment device comprising:

a dialyzer including a blood chamber and a dialysate chamber separated by a semipermeable membrane, the blood chamber being capable of being connected to a dialysis patient via an extracorporeal blood circulation path, blood flowing in and out of the blood chamber at blood flow rate, the dialysate chamber being connected to a dialysate circuit, dialysate flowing in and out of the dialysate chamber at a dialysate flow rate;

at least one sensor for measuring a concentration of a substance in dialysate flowing out of the dialyzer, at least one of the at least one sensor being disposed downstream from the dialyzer;

an interrupting device for interrupting dialysate flow through the dialyzer;

a control/analyzer unit connected to the interrupting device for receiving at least an output measurement signal of the at least one sensor, the control/analyzer unit be capable of, at a time when the concentration of the substance in blood of a patient is determined, sending a signal to the interrupting device so that there is no flow in the dialysate chamber and a residual dialysate is maintained in the dialysate chamber, and, after a preset time interval to establish a steady state so that at least part of the residual dialysate substantially adopts the concentration of the substance in blood flowing into the blood chamber, of sending a signal to the interrupting device for reconnecting the dialyzer to the dialysate circuit to flush out the residual dialysate, and then, after a time interval determined by a flow rate of the dialysate and a distance of an outlet of the dialyzer from the at least one sensor, of analyzing the output measurement signal of the at least one sensor to determine the concentration of the substance in the residual dialysate.

26. A device as recited in claim 25 further comprising a bypass line for bridging the dialysate chamber when the dialysate flow is interrupted.

27. A device as recited in claim 25 wherein the control/analyzer unit is capable of sending a signal for measuring a concentration of the substance in the dialysate upstream of the dialyzer and a concentration of the substance in the dialysate downstream of the dialyzer, and of sending a signal for restoring flow in the dialysate chamber, and wherein a timing control on the control/analyzer unit is set so that after a determination of the concentration of the substance in the blood flowing into the blood chamber and a reconnection of the dialyzer to the dialysate circuit, the control/analyzer unit is capable of analyzing, as measurement signals, signals for dialysate flow rate and signals for the concentration of the substance in the dialysate flowing into and flowing out of the dialyzer, and is capable of determining a dialysance using the equation $$D = Q_d \cdot \frac{c_{do} - c_{di}}{c_{bi} - c_{di}}$$

where:

D=the dialysance $Q_d$=the dialysate flow rate $c_{do}$=the concentration of the substance in the dialysate flowing out of the dialysate chamber $c_{di}$=the concentration of the substance in the dialysate flowing into the dialysate chamber $c_{bi}$=the concentration of the substance in the blood flowing into the blood chamber.

28. The device as recited in claim 25 wherein the at least one sensor comprises at least one of a conductivity sensor and an optical sensor.

* * * * *